(12) United States Patent
Maarek

(10) Patent No.: US 10,383,565 B2
(45) Date of Patent: Aug. 20, 2019

(54) METHOD AND APPARATUS TO ASSESS EARLY STAGES OF PERIPHERAL DISTAL NEUROPATHY IN DIABETIC PATIENTS

(71) Applicant: Medical Screening Corporation, Miami, FL (US)

(72) Inventor: Albert Maarek, Miami, FL (US)

(73) Assignee: Medical Screening Corporation, Miami, FL (US)

( * ) Notice: Subject to any disclaimer, the term of this patent is extended or adjusted under 35 U.S.C. 154(b) by 697 days.

(21) Appl. No.: 14/814,643

(22) Filed: Jul. 31, 2015

(65) Prior Publication Data

US 2015/0335277 A1 Nov. 26, 2015

Related U.S. Application Data

(63) Continuation-in-part of application No. PCT/IB2014/001047, filed on Jun. 12, 2014.

(60) Provisional application No. 61/835,064, filed on Jun. 14, 2013.

(51) Int. Cl.
| | | |
|---|---|---|
| *A61B 5/02* | (2006.01) | |
| *A61B 5/00* | (2006.01) | |
| *A61B 5/0295* | (2006.01) | |
| *A61B 5/053* | (2006.01) | |

(52) U.S. Cl.
CPC .......... *A61B 5/4041* (2013.01); *A61B 5/0295* (2013.01); *A61B 5/0531* (2013.01); *A61B 5/415* (2013.01); *A61B 5/4266* (2013.01); *A61B 5/7282* (2013.01); *A61B 2562/0214* (2013.01)

(58) Field of Classification Search
CPC ......... A61B 5/05; A61B 5/4041; A61B 5/053; A61B 5/4029
See application file for complete search history.

(56) References Cited

U.S. PATENT DOCUMENTS

| | | |
|---|---|---|
| 3,399,666 A | 9/1968 | Broach |
| 3,794,910 A | 2/1974 | Ninke et al. |
| 8,934,954 B2 | 1/2015 | Brunswick |
| 2011/0190745 A1 | 8/2011 | Uebelhoer et al. |
| 2013/0317318 A1* | 11/2013 | Tartz .................... A61B 5/6843 600/301 |
| 2013/0324814 A1 | 12/2013 | Maarek |

(Continued)

FOREIGN PATENT DOCUMENTS

| | | |
|---|---|---|
| WO | 2011070422 A1 | 6/2011 |
| WO | 2012076957 A1 | 6/2012 |

OTHER PUBLICATIONS

Low, V.A., et al., Detection of small-fiber neuropathy by sudomotor testing., Jul. 2006, pp. 57-61, 34(1), Muscle & Nerve.

(Continued)

*Primary Examiner* — Puya Agahi
(74) *Attorney, Agent, or Firm* — Mark Terry

(57) ABSTRACT

A method and apparatus to assess sudomotor function to detect early stage peripheral distal neuropathy. The method sends a low voltage direct current of 1 to 5 volts between pairs of electrodes for a time of between 15 and 60 seconds, switches the current at the middle of the time and measures the peak and slope of the decreased conductance. The method can be used to assess skin blood flow and/or sweat gland density depending on the direction of the current.

5 Claims, 2 Drawing Sheets

(56) References Cited

U.S. PATENT DOCUMENTS

Figure 1:
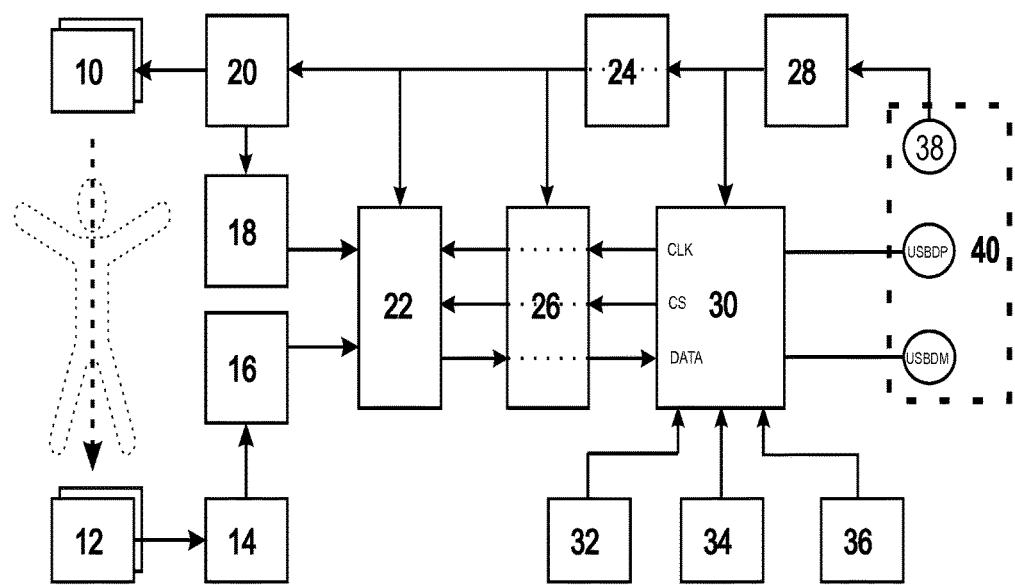

2015/0250404 A1 9/2015 Maarek
2015/0313477 A1 11/2015 Maarek

OTHER PUBLICATIONS

Girach, A., et al., Diabetic microvascular complications: can patients at Risk be Identified? A Review., Nov. 2006, pp. 1472-1483, Int J Clin Pract.

Shahani, B T, et al., Sympathetic skin response—a method of assessing unmyelinated axon dysfunction in peripheral neuropathies, 1984, pp. 536-542, 47, Journal of neurology, Neurosurgery, and Psychiatry.

Schlereth, T., et al., Somatotopic arrangement of sudomotor axon reflex sweating in humans., 2005, pp. 76-81, 123, AutonomNeurosci.

Gibbons, C.H., et al., Quantification of sweat gland innervation: a clinical-pathologic correlation., 2009, pp. 1479-1486, 72, Neurology.

Sommer, P., et al., Electrically induced quantitative sudomotor axon reflex test in human volunteers., 2011, pp. 111-116, 159, Autonomic Neuroscience: Basic and Clinical.

Hashimoto, K., Demonstration of the intercellular spaces of the human eccrine sweat gland by lanthanum. I. The secretory coil., 1971, pp. 249-262, 36, J Ultrastruct Res.

Stanley, EF., et al., Single calcium channels and acetylcholine release at presynaptic nerve terminal., 1993, pp. 1007-1011, 11(6), Neuron.

Mishra, A., et al., The Relevance of Sweat Testing for the Diagnosis of Cystic Fibrosis in the Genomic Era., 2005, pp. 135-153, 26(4), Clin Biochem Rev.

Grimmes, S., et al., Electrolytics. In: Bioimpedance and Bioelectricity Basics., 2008, Academic Press, Maryland Heights, MO.

Gibbons, et al., Quantitative direct and indirect test of sudomotor function, Jun. 10, 2008, pp. 2299-2304, 70(24), Neurology (online).

\* cited by examiner

METHOD AND APPARATUS TO ASSESS EARLY STAGES OF PERIPHERAL DISTAL NEUROPATHY IN DIABETIC PATIENTS

The present invention relates to an improved method to assess sudomotor function. More specifically the invention relates to a method and apparatus to assess early stages of peripheral distal neuropathy in diabetic patients.

Sudomotor function is controlled by part of the sympathetic nervous system (post sympathetic cholinergic fiber) and it relates to skin blood flow and small demyelinated nerve fibers (C-Fibers) controlling the activity of sweat glands.

Sudomotor dysfunction is used to define a decreased sudomotor activity. Traditional neurophysiologic measurements of sudomotor function include thermoregulatory sweat testing (TST), quantitative sudomotor axon reflex testing (QSART), silicone impressions and sympathetic skin response (SSR).

C-Fiber damage leads to small fiber neuropathy and reduced peripheral blood flow leads to microcirculation disorders.

People with diabetes are at increased risk of microcirculation disorders and small fiber neuropathy that are the early stages of peripheral distal neuropathy, as well as having a higher risk of developing infections and decreased ability to clear infections. Therefore, people with diabetes are prone to frequent and often, severe peripheral distal neuropathy (most frequently in the feet) with a relatively high risk of infection, gangrene and amputation.

Peripheral distal neuropathy progressively affects the skin nerves which comprise C-Fibers first line because they are unprotected, then, A delta fibers, A-Alpha and Beta and finally large motor fibers.

Mainly, sudomotor function evaluation is a screening test for small fiber neuropathy and related symptoms and pains[1].

Small fiber neuropathy could be the earliest stages of peripheral distal neuropathy in populations at high risk such as diabetic patients. In addition, sudomotor dysfunction has been found in different diseases or as medication side effects such as with cancer treatment, antihypertensive treatment (in particular beta and alpha blockers and calcium antagonists), metformin treatment, vitamin deficiency, Parkinson's disease, AIDS, amyotrophic lateral sclerosis, hypothyroidism, kidney and liver diseases, alcoholism, Alzheimer's disease and Guillain-Barre syndrome.

The evolution of peripheral foot neuropathy comprises 4 steps.

Step 1: Microcirculation disorder and decreased skin blood flow.

Step 2: Decreased sweat gland function related to the C-Fiber damage.

Step 3: Progressive damage of the other skin nerves (A delta fibers, A-Alpha and Beta and finally large motor fibers).

Step 4: Necrosis and potentially amputation.

Steps 1 and 2 are reversible with effective treatment, unlike the steps 3 and 4 that have only palliative treatment.

To assess sudomotor function, an electrical output signal is sent to the skin in contact with the active receiving electrode with a voltage lower than 5 V.

The signal is carried by the interstitial fluid ions or axon reflex through the body to reach the skin in contact with the passive responsive electrode. In the skin, the signal provokes an electrical stimulation of the post-sympathetic cholinergic fiber (C Fiber)[6] that releases acetylcholine.[4]

Acetylcholine stimulates the nicotinic muscarinic receptors (M receptors).[4]

The activation of M receptors will have 2 effects:

1. Effect on skin blood flow: Activation of M3 on vascular endothelial cells causes increased synthesis of nitric oxide (NO), which diffuses to adjacent vascular smooth muscle cells and causes their relaxation and vasodilation.[2]

2. Effect on the sweat glands function: Activation of Inositol polyphosphates (IPP's) causes intracellular calcium mobilization and calcium influx.[8] The increased cytoplasmic calcium stimulates chloride channels in the apical (luminal) membrane, and potassium channels in the basolateral membrane of the secretory clear cell of the sweat glands, resulting in the efflux of both ions.[8] Chloride enters the secretory cell via either a Na-2Cl—K or Na—Cl cotransport system, and leaves the cells by diffusion into the lumen of the sweat duct.[7] The movement of chloride across the apical membrane depolarizes the apical membrane and generates a negative luminal potential. This negative lumen charge then attracts sodium into the lumen across the intercellular junction (i.e. paracellular pathway).[9]

The two effects of the electrical stimulation process generate electrochemical reactions on the bulk of the passive responsive electrode.[10]

It is an object of the present invention to provide a new method of testing that will allow separate assessment of skin blood flow, and the overall induced sweat output.

It is a particular aim of the present invention to provide a new method of measurement that can detect the early phases 1 (decreased skin blood flow) and 2 (decreased sweat gland function) of the peripheral distal neuropathy when treatment could be effective and could reverse disease evolution to ulcer, necrosis and amputation.

According to the present invention there is provided an improved method to evaluate sudomotor function of an individual, the method comprising the steps of sending a low constant voltage direct current between 1 to 5 volts from a positive or negative electrode to a contralateral electrode with the electrodes placed on 2 separate skin areas of an individual for a time of between 15 to 60 seconds and switching the voltage during the measurement.

In a first embodiment the method comprises sending the current from negative to positive electrode and switching the voltage during the time and measuring in the negative electrode the slope of the following decrease of Peak conductance or voltage to assess the skin blood flow.

In an alternative embodiment the current is sent from positive to negative electrode and switching the voltage during the time and measuring in the positive electrode the peak of conductance or voltage and the slope of the following decrease of Peak conductance or voltage to assess sweat gland function.

Most preferably the method of the invention comprises both of the embodiments as set out above carried out consecutively.

In a particularly preferred embodiment the method comprises the steps of 1) sending a low constant voltage direct current between 1 to 5 volts from negative to positive electrode for a time of between 15 and 60 seconds, switching the current at the middle time and measuring the slope of the following decrease of Peak conductance or voltage, and 2) sending a constant low voltage direct current between 1 to 5 volts from positive to negative electrode for a time of between 15 and 60 seconds, switching the current at the middle time and measuring the amplitude of the resulting peak of conductance or voltage and the slope of the following decrease of Peak conductance or voltage.

Preferably the low constant voltage direct current is between 1 to 5 volts.

More preferably the current is 1.28 or 1.64 Volts.

In one preferred embodiment the low voltage direct current is 1.28V.

The invention also provides an apparatus comprising electrodes, hardware and software to carry out the method as described.

Preferably the electrodes are placed on the soles of the feet areas with a large density of sweat glands.

Preferably the electrodes are in reusable stainless steel or Silver/Silver Chloride disposable electrodes (Ag/AgCl).

Preferably the electrochemical reactions on the bulk of the active electrode are measured in conductance expressed in micro-Siemens ($\mu$Si) units or voltage expressed in milliAmperes (mA).

Stage 1 of peripheral neuropathy can be detected when the peak of conductance after switching the voltage from positive to negative electrode is less than 65 $\mu$Si or 0.83 Volt.

Stage 2 of peripheral neuropathy can be detected when the peak of conductance after switching the voltage from negative to positive electrode is less than 90 $\mu$Si or 1.23 Volts and the slope of the following decrease of Peak conductance is less than 65 $\mu$Si or 0.83 Volt.

The invention further provides as score for early detection of peripheral neuropathy using the three conductance measurements.

Figure 2:
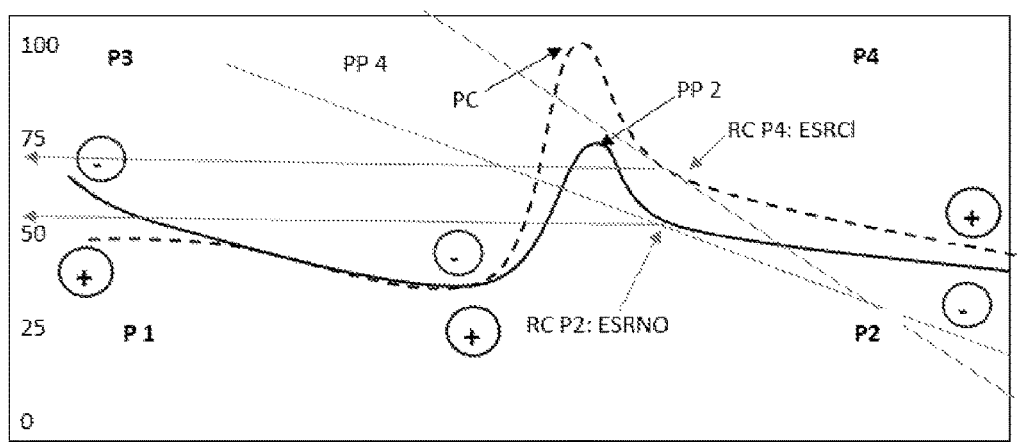

The invention is further described with reference to the accompanying non limiting figures wherein FIG. 1 is a flow diagram of the apparatus and steps in a preferred embodiment of the invention FIG. 2 shows the traces generated in the phases of the measurement including the peak and slopes.

HARDWARE

With reference to the diagram of FIG. 1, in a preferred embodiment of the apparatus the device has 2 to 8 tactile electrodes placed on skin areas with the highest sweat gland density. Each electrode can be active (10) or passive (12) and sequence and polarity are both managed by the software. There is a filter of low frequency (14), repeaters (16), (18), a reference voltage unit (20), analog-digital converter (ADC—serial type AD7828) (22), electrical isolation (24), electrical isolation (26) to digital buses, high frequency filter (28), USB-controller (30), generator (32), circuit (34), memory (ROM) (36), power bus (38) and USB connectors (40) to the USB-port of the computer.

Signal Pathway:

Block (20) generates the reference voltage signal (from 1.28 V to 4V), in DC or frequency <100 Hz that is fed to the active electrode (10) that is connected to the skin of the patient. Then the signal passes through the liquid compartment of the patient and reaches the skin in contact with passive electrode (12). The noise is filtered, by passing through the low frequency filter (14) and then through repeaters (16, 18) providing galvanic isolation and then the signal processing analysis is performed at the analog-digital converter (ADC) (22). ADC converts the signal to digital code. The digital code goes through a galvanic isolation (26) to USB controller (30) and then is released to the slot (40) of the USB port of the computer for the further processing analysis by the software.

The invention provides a new process to assess two components of the sudomotor pathway using hardware and software (SudoPath system) in order to screen the early stages of peripheral distal neuropathy in diabetic patients.

The invention is a new improved process. The method uses pair(s) of tactile electrodes and is performed by electrical stimulation of the skin via passive electrode and contralateral electrical stimulation of the skin capillaries and C-fibers that provoke hyperemia and exit of water and ions on the bulk of the active electrode. The exit of water and ions provoke an electrochemical reaction that is measured as a current in millivolts or milliAmperes or resistance or conductance.

The software receives the digital code of the ADC and can display the values in a graphic as shown in FIG. 2.

During the measurement, the software controls the sequence for each electrode activation and the polarity of the signal (electrical stimulation).

Phase 1 (P1): the voltage is sent from negative electrode (−) to positive electrode (+). The voltage is positive.

Phase 2 (P2): the polarity of the voltage is switched from positive (+) to negative (−) electrode, the voltage is negative, there is no ion migration and the release of NO increases the skin blood flow and the slope of the decrease of conductance of the peak in phase 2 is detected in the graphic: The slope of the decreased of conductance of the peak in phase 2 reflects the blood flow of the skin in contact with the negative electrode. We named the slope of conductance in phase 2 Electro Skin Response Nitric oxide (ESRNO).

Phase 3: (P3) the current is sent from positive electrode (+) to negative (−) electrode. The voltage is negative.

Phase 4: (P4) the polarity of the voltage is switched from negative (−) to positive (+) electrode, the voltage is positive, the negative ions (preferably OH—) migrated and a peak of conductance is detected in the graphic as well as the slope of the decreased of conductance in phase 4.

The peak of conductance of the phase 4 and the slope of the decreased of conductance in phase 4 reflects the sweat gland function in the skin in contact with the positive electrode. We named the peak of conductance value Peak C (PC) and the slope of conductance in phase 4 Electro Skin Response negative ions (ESR i−).

In summary, the present invention is based upon the switch of polarity of the voltage during the measurement of each pathway between the pairs of electrodes and this method allows the possibility to separate the 2 effects of the electrical stimulation of the C-Fiber.

Normal range of the 3 measured markers was evaluated in clinical studies with a supposed population without skin blood flow decreased or sweat function reduced ESRNO Normal range is greater than 65 $\mu$Si or 0.83 Volt
ESR i− Normal range is greater than 65 $\mu$Si or 0.83 Volt Peak C Normal range is greater than 90 $\mu$Si or 1.23 Volts No differences were found according to gender and weight or height of the tested population. However, elderly subjects have a lower voltage comparing to the young subjects (average of 15%).

ESRNO less than 65 $\mu$Si suggests skin blood flow is decreased and phase 1 of peripheral distal neuropathy in diabetic patients and ESR i− less than 65 $\mu$Si or Peak C less than 90 $\mu$Si i suggest reduced sweat gland function and phase 2 of peripheral distal neuropathy in diabetic patients. Both of these conditions suggest early signs of peripheral distal neuropathy and causes should be considered and appropriate action taken to prevent further nerve damage and the need for more disruptive treatments in the future.

Early stage (1 and 2) of peripheral distal neuropathy score

A Sudomotor Response (SMR) score is calculated using the 3 markers of the invention Each marker is scored as follow:
ESRNO>=65 µSi=>Score=0
ESRNO<65 and >=40 µSi ï=>Score=1
ESRNO<40 µSi=>Score=2
ESR i->=65 µSi=>Score=0
ESR i-<65 and <=40 µSi=>Score=1
ESR i-<40 µSi ï=>Score=2
Peak C>=90 µSi=>Score=0
Peak C>90 and >=70 µSi=>Score=1
Peak C<70 µSi=>Score=2

The SMR Score is the sum of the score of each marker. The score can also be displayed as a number of as percent scale from 0 to 100.

Clinical Study 1

New approach in Type 2 Diabetes treatment management and early detection of complications.

Pratiksha G Gandhi, Cardiologist, Mumbai, India
Pr Gundu H. R. Rao, Ph.D University of Minnesota Summary Background: Since type 2 diabetes has become a pandemic disease in the last 10 years, and lab tests methods have failed in screening of diabetes and to detect complications before onset, this study aims to evaluate markers for diabetes by assessing endothelial function and autonomic nervous system.

Materials and Method:

One hundred sixty four patients were included in the study.

The patients were separated in 4 groups:

Group 1: One hundred two patients (70 males), with the mean age of 56 years (range 26-90), BMI 29 who were diagnosed with type 2 diabetes and undergoing treatment.

Group 2: Subgroup of Group 1 comprised of twenty-five patients (16 males) with mean age of 66 years (range 56-88) and had signs and symptoms of peripheral neuropathy such as tingling, burning or electric-like pain or extreme sensitivity to touch in feet.

Group 3: Subgroup of Group 1, comprised of sixty-seven patients (42 males) with mean age of 45 years (range 25-85) but did not have signs or symptoms of peripheral neuropathy.

Group 4: Sixty-two patients with the mean age of 40 years (range 22-85) who are in healthy condition, have had no diagnosis of diabetes or signs/symptoms of foot neuropathy or autonomic neuropathy.

All groups of patients underwent examination with the TM-Oxi and SudoPath system at IPC Heart Care Centre (Mumbai, India) for assessing autonomic nervous system and endothelial function. The SudoPath system uses a galvanic skin response technology to assess post sympathetic cholinergic fiber in order to detect skin microcirculation disorders (ESRNO) and sweat gland density (ESRC1 and PeakC). The system provides a Sudomotor Response Score (SMR Score) based on these 3 parameters for early detection of peripheral neuropathy.

Statistical analysis was performed using Receiver-Operating Characteristic (ROC) curves to determine the specificity and sensitivity of markers and scoring system comparing diabetic group and healthy subjects as well as diabetic subgroups with symptoms and without symptoms.

Results:

Comparing the diabetes patients group (group 1) and healthy subjects (group 4) ESRNO returned a sensitivity of 68.6% and specificity of 87.1% (cutoff #>49) (P=0.0001). Area under the Roc curve (AUC)=0.865.

Comparing the diabetes subgroups with symptoms of peripheral neuropathy (group 2) and the diabetes patients group without symptoms of foot neuropathy (group 3), SMR Score had a sensitivity of 91.4% and specificity of 79.1% (cutoff #>3) to detect foot neuropathy symptoms in diabetic patients (P=0.0001). Area under the Roc curve (AUC) =0.858.

Conclusion:

In conclusion, SudoPath will be useful to assess the susceptibility of patients with type 2 diabetes to develop peripheral neuropathy, thus reducing the occurrence of these complications in the long term.

Clinical Study 2 (Updated Study)

Gandhi P G, Rao G H. Detection of neuropathy using a sudomotor test in type 2 Diabetes. Degenerative Neurological and Neuromuscular Disease. January 2015, 5:1-7

Summary

Background: The sudomotor test is used to evaluate the postganglionic cholinergic sympathetic nervous system. The aim of this study was to evaluate the efficacy of a sudomotor testing device to detect peripheral distal neuropathy (PDN) and cardiac autonomic neuropathy (CAN) in patients with type 2 diabetes.

Materials and methods: A total of 133 type 2 diabetic patients were included in the study. The patients underwent examination at the IPC Heart Care Centre (Mumbai, India) in order to assess the diabetic neuropathy symptoms (DNS) score, using a questionnaire and the CAN score, using heart rate variability analysis and Ewing tests. In addition, patients were given a sudomotor test using the SudoPath™ system. The diagnosis of PDN is based on the DNS score. A DNS score of 1 or higher is defined as a positive result for PDN. According to the DNS score, the patients were separated into two groups: Group 1 comprised 35 patients (21 males), with the mean age of 66 years (standard deviation [SD]=12.1), who had a DNS score ≥1. Group 2 comprised 98 patients (65 males), with the mean age of 56 years (SD=9.6), who had a DNS score=0. The SudoPath system is a galvanic skin response device that uses the quantitative sudomotor axon reflex approach to assess for small and unmyelinated fiber neuropathy. The system provides a sudomotor response (SMR) score based on these three measured sudomotor parameters. A statistical analysis was performed using the analysis of variance to compare mean differences between the groups as well as receiver operating characteristic (ROC) curves, to determine the specificity and sensitivity of SMR score to detect PDN, comparing the diabetic groups 1 and 2, and the coefficient of correlation between the CAN score and the SMR score in all the subjects included in the study.

Results: When comparing the diabetes groups 1 and 2, the SMR Score had a sensitivity of 91.4% and specificity of 79.1% (cutoff number >3) to detect PDN (P=0.0001). Area under the ROC curve (AUC)=0.893. A correlation analysis of the CAN score and SMR score returned a coefficient of correlation r=0.68 (P<0.0001).

Conclusion: The SudoPath system is easy to use, operator-independent, and fast (3-minute testing time). This study shows that the device will be useful to assess the susceptibility of type 2 diabetes patients in developing PDN complications.

REFERENCES

1. Low V Al, Sandroni P, Fealey R D, Low P A. Detection of small-fiber neuropathy by sudomotor testing. Muscle Nerve. 2006 July; 34(1):57-61.
2. Girach A, Manner D, Porta M. Diabetic microvascular complications: Can patients at risk be identified? A review. Int J Clin Pract.

3. Shahani B T, Halperin J. J, Boulu P, Cohen J. Sympathetic skin response-a method of assessing unmyelinated axon dysfunction in peripheral neuropathies. Journal of Neurology, Neurosurgery, and Psychiatry 1984; 47:536-542
4. Schlereth T, Brosda N, Birklein F. Somatotopic arrangement of sudomotor axon reflex sweating in humans. AutonomNeurosci. 2005; 123:76-81.
5. Gibbons, C. H., Illigens, B. M., Wang, N., Freeman, R., 2009. Quantification of sweat gland innervation: a clinical-pathologic correlation. Neurology 72, 1479-1486.
6. Sommer P, Kluschina O, Schley M, Namer B, Schmelz M, Rukwied R. Electrically induced quantitative sudomotor axon reflex test in human volunteers. Autonomic Neuroscience: Basic and Clinical 159 (2011) 111-116.
7. Hashimoto K. Demonstration of the intercellular spaces of the human eccrine sweat gland by lanthanum. I. The secretory coil. J Ultrastruct Res. 1971; 36:249-262.
8. Stanley E F. Single calcium channels and acetylcholine release at a presynaptic nerve terminal. Neuron. 1993 December; 11(6): 1007-11.
9. Mishra A, Greaves R, and Massie J. The Relevance of Sweat Testing for the Diagnosis of Cystic Fibrosis in the Genomic Era. Clin Biochem Rev. 2005 November; 26(4): 135-153.
10. Grimmes S, Martinsen 0G. Electrolytics. In: Bioimpedance and Bioelectricity Basics. Maryland Heights, Mo.: Academic Press; 2008.

I claim:

1. A device for detecting early stages of peripheral neuropathy, comprising:
    a set of 2 to 8 tactile electrodes configured for placement on a patient's skin, wherein each tactile electrode is configured for operating both as an active and a passive electrode;
    a low frequency filter coupled to one or more tactile electrodes of the set of tactile electrodes, wherein the low frequency filter generates a reference voltage signal from 1.28 V to 4 V direct current or alternating current at a frequency less than 100 Hz;
    a computing device communicatively coupled with said set of tactile electrodes, the computing device configured for controlling a polarity and a sequence of activation of each tactile electrode, the computing device further configured for:
        designating at least one of the set of tactile electrodes as a positive electrode and designating at least one of the set of tactile electrodes as a negative electrode;
        applying a voltage via the low frequency filter from the positive electrode to the negative electrode and measuring peak conductance after switching the voltage from the positive electrode to the negative electrode, wherein if the peak conductance after switching the voltage from the positive electrode to the negative electrode is less than 65 micro Siemens or 0.83 Volts, then determining that stage 1 peripheral neuropathy is detected, and displaying said determination; and
        applying a voltage via the low frequency filter from the negative electrode to the positive electrode and measuring peak conductance after switching the voltage from the negative electrode to the positive electrode, wherein if the peak conductance after switching the voltage from the negative electrode to the positive electrode is less than 90 micro Siemens or 1.23 Volts, then determining that stage 2 peripheral neuropathy is detected, and displaying said determination.

2. The device as claimed in claim 1, the computing device further configured for:
    applying a constant low voltage direct current from the positive electrode or the negative electrode to a contralateral electrode placed on 2 separate skin areas of the patient for a time period between 15 to 60 seconds; and
    switching the low voltage direct current at a midpoint of the time period and analyzing changes in conductance, voltage, intensity or resistance.

3. A device as claimed in claim 1, the computing device further configured for:
    performing electrical skin stimulation according to the following sequence: applying a voltage from the negative electrode to the positive electrode, switching polarity of the voltage that was applied from the negative electrode to the positive electrode, applying a current from the positive electrode to the negative electrode and switching the polarity of the voltage from the negative electrode to the positive electrode.

4. A device as claimed in claim 1, the computing device further configured for:
    generating a score for detection of peripheral neuropathy based on the peak conductance that was measured.

5. A device as claimed in claim 4, the computing device further configured for
    wherein if the score that was generated is greater than 50% of a total possible score, then determining that stage 1 peripheral neuropathy and/or stage 2 peripheral neuropathy has been detected in a diabetic patient, and displaying said determination.

* * * * *